(12) United States Patent
Takenaka et al.

(10) Patent No.: US 10,009,990 B2
(45) Date of Patent: Jun. 26, 2018

(54) IMAGING APPARATUS, CONTROL METHOD THEREFOR, AND IMAGING SYSTEM

(75) Inventors: Katsuro Takenaka, Honjo-shi (JP); Toshio Kameshima, Kumagaya (JP); Tomoyuki Yagi, Honjo (JP); Sho Sato, Saitama (JP); Atsushi Iwashita, Saitama (JP); Eriko Sugawara, Honjo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 55 days.

(21) Appl. No.: 14/118,775

(22) PCT Filed: Apr. 19, 2012

(86) PCT No.: PCT/JP2012/061159
§ 371 (c)(1),
(2), (4) Date: Dec. 13, 2013

(87) PCT Pub. No.: WO2012/160935
PCT Pub. Date: Nov. 29, 2012

(65) Prior Publication Data
US 2014/0112448 A1    Apr. 24, 2014

(30) Foreign Application Priority Data

May 24, 2011 (JP) .................................. 2011-116271

(51) Int. Cl.
*G01T 1/24* (2006.01)
*G01T 1/29* (2006.01)
(Continued)

(52) U.S. Cl.
CPC ............... *H05G 1/56* (2013.01); *H04N 5/32* (2013.01); *H04N 5/347* (2013.01); *H04N 5/353* (2013.01);
(Continued)

(58) Field of Classification Search
CPC ........................... H04N 5/3456; H04N 5/347
(Continued)

(56) References Cited

U.S. PATENT DOCUMENTS 5,894,129 A    4/1999  Pool ........................ 250/370.09
6,243,441 B1   6/2001  Zur .............................. 378/98.8
(Continued)

FOREIGN PATENT DOCUMENTS

JP    09-107503 A    4/1997
JP    2001-116846 A  4/2001
(Continued)

OTHER PUBLICATIONS

European Communication issued in counterpart application No. 12789344.4 dated Nov. 14, 2014 (7 pages).
(Continued)

*Primary Examiner* — Carolyn Igyarto
(74) *Attorney, Agent, or Firm* — Fitzpatrick, Cella, Harper & Scinto

(57) ABSTRACT

An imaging apparatus comprises a detecting unit for converting radiation or light into an electric signal provided with a plurality of pixels arranged in a matrix, each of the pixels including a conversion element and a switching element, a drive circuit unit for controlling a conducting state of the switching element, and a control circuit unit for controlling the drive circuit unit based on the electric signal converted by the detecting unit. The control circuit unit controls the drive circuit unit to perform steps including the drive circuit unit setting the switching elements at the conducting state row by row to acquire an offset image based on the signal accumulated in the plurality of pixels for subtraction processing of the image.

13 Claims, 11 Drawing Sheets

(51) Int. Cl.
    *H05G 1/56*     (2006.01)
    *H04N 5/32*     (2006.01)
    *H04N 5/347*    (2011.01)
    *H04N 5/353*    (2011.01)
    *H04N 5/374*    (2011.01)
    *H04N 5/378*    (2011.01)
    *A61B 6/00*     (2006.01)

(52) U.S. Cl.
    CPC ........... *H04N 5/378* (2013.01); *H04N 5/3742* (2013.01); *A61B 6/4283* (2013.01); *A61B 6/4405* (2013.01)

(58) Field of Classification Search
    USPC ................. 250/370.08, 370.09, 370.14, 371; 378/116
    See application file for complete search history.

(56) References Cited

U.S. PATENT DOCUMENTS

| | | | |
|---|---|---|---|
| 6,404,854 B1 | 6/2002 | Carroll et al. | |
| 6,801,598 B2 | 10/2004 | Tashiro et al. | 378/98.8 |
| 7,227,926 B2 | 6/2007 | Kameshima et al. | |
| 7,343,000 B2 | 3/2008 | Kameshima et al. | |
| 7,403,594 B2 | 7/2008 | Endo et al. | |
| 7,408,167 B2 | 8/2008 | Kameshima et al. | |
| 7,442,939 B2 | 10/2008 | Yagi et al. | |
| 7,541,591 B2 | 6/2009 | Endo et al. | |
| 7,564,038 B2 | 7/2009 | Endo et al. | |
| 7,573,041 B2 | 8/2009 | Kameshima et al. | |
| 7,786,448 B2 | 8/2010 | Endo et al. | |
| 7,791,034 B2 | 9/2010 | Kameshima et al. | |
| 7,869,568 B2 | 1/2011 | Yokoyama et al. | |
| 7,994,481 B2 | 8/2011 | Yagi et al. | |
| 8,107,588 B2 | 1/2012 | Kameshima et al. | |
| 2002/0122123 A1* | 9/2002 | Kimura | 348/246 |
| 2005/0220268 A1 | 10/2005 | Fujii et al. | |
| 2011/0309262 A1 | 12/2011 | Sato et al. | |
| 2011/0317054 A1 | 12/2011 | Kameshima et al. | |
| 2013/0032696 A1 | 2/2013 | Tajima | |
| 2013/0140467 A1 | 6/2013 | Kitano et al. | 250/393 |
| 2013/0264488 A1 | 10/2013 | Sugawara et al. | |
| 2014/0061491 A1 | 3/2014 | Iwashita et al. | |
| 2014/0185764 A1 | 7/2014 | Takenaka et al. | |
| 2014/0239186 A1 | 8/2014 | Sato et al. | |
| 2014/0239187 A1 | 8/2014 | Iwashita et al. | |
| 2014/0241501 A1 | 8/2014 | Sato et al. | |
| 2014/0241506 A1 | 8/2014 | Iwashita et al. | |
| 2014/0285689 A1 | 9/2014 | Ryu et al. | |

FOREIGN PATENT DOCUMENTS

| | | | |
|---|---|---|---|
| JP | 2002-281389 A | 9/2002 | |
| JP | 2002-369078 A | 12/2002 | |
| JP | 2003-126072 A | 5/2003 | |
| JP | 2005-143802 A | 6/2005 | |
| JP | 2008-132216 A | 6/2008 | |
| WO | 2011135917 A1 | 11/2011 | |
| WO | WO 2012/008229 A1 | 1/2012 | |

OTHER PUBLICATIONS

Japanese Office Action issued in counterpart application No. 2011-116271 dated Feb. 24, 2015, along with its English-language translation (5 pages).

* cited by examiner

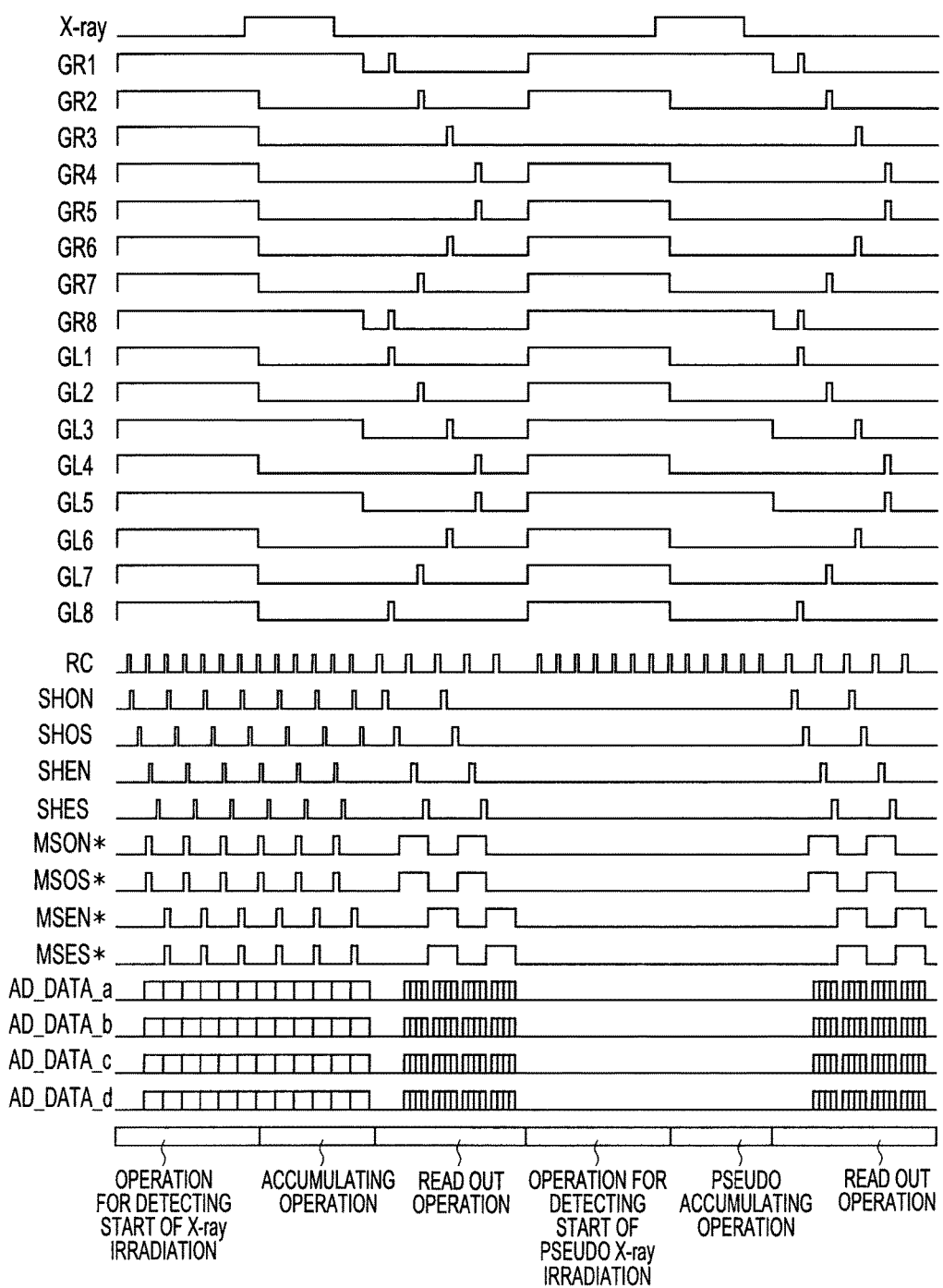

IMAGING APPARATUS, CONTROL METHOD THEREFOR, AND IMAGING SYSTEM

TECHNICAL FIELD

The present invention relates to an imaging apparatus and a control method therefor suitable for use in medical diagnosis and industrial non-destructive inspection. In particular, the present invention relates to an imaging apparatus, a control method therefor, and an imaging system having a detecting unit provided with a plurality of pixels arranged in a matrix, each pixel including a conversion element for converting radiation or light to an electric charge and including a switch element for outputting an electric signal based on the electric charge.

BACKGROUND ART

In recent years, as an imaging apparatus for use in medical image diagnosis and non-destructive inspection using X rays, a radiation imaging apparatus using a flat panel detector (hereinafter referred to as an FPD) made of a semiconductor material has been put into practical use. The radiation imaging apparatus with an FPD is an apparatus capable of digital imaging by using the FPD to convert radiation, such as X-ray, transmitted through an object, such as a patient, to an analog electrical signal and converting the signal in analog/digital conversion to obtain a digital image signal. For example, in medical image diagnosis, such a radiation imaging apparatus with an FPD has been used as a digital imaging apparatus for still image radiographing such as radiography and moving image radiographing such as fluoroscopic imaging.

In order to use such an imaging apparatus in X-ray imaging, X-ray irradiation by an X-ray generating apparatus needs to be synchronized with operation of the imaging apparatus. Specifically, in response to the start of X-ray irradiation, the imaging apparatus needs to start the accumulation operation of accumulating electrical signals based on X-ray transmitted through the object. In response to the end of the X-ray irradiation, the imaging apparatus needs to start the read operation of reading the accumulated electrical signals.

Examples of the method of synchronizing the X-ray irradiation by the X-ray generating apparatus with the operation of the imaging apparatus include a method of using a cable to connect the X-ray generating apparatus to the imaging apparatus; and a method of causing the imaging apparatus to detect X-ray irradiation without a cable and starting the operation of the imaging apparatus in response to the detected X-ray irradiation.

As the method of detecting X-ray irradiation by the imaging apparatus, for example, there have been known techniques disclosed in the following Patent Literature 1 and Patent Literature 2. Patent Literature 1 describes a technique in which when X-ray irradiation is detected, neighboring pixel signals are added and the added signals are sequentially read. Patent Literature 2 describes a technique in which arbitrarily selected determination pixel signals are sequentially read to detect X-ray irradiation.

CITATION LIST

Patent Literature

PTL 1: Japanese Patent Application Laid-Open No. 2001-116846

PTL 2: Japanese Patent Application Laid-Open No. 2005-143802

SUMMARY OF INVENTION

Technical Problem

The aforementioned detection of X-ray irradiation needs to detect X-ray irradiation in a condition without an object for detection or in a region with a large amount of transmitted X-ray from the object for detection. Unfortunately, it is unknown before imaging how the object is arranged. Thus, X-ray needs to be detected in a wide region of the detecting unit. Further, the imaging apparatus uses a flat panel detector made of a semiconductor material. Thus, an increase in accumulation time increases dark current which deteriorates image quality. Accordingly, an X-ray pulse width (from the start of irradiation to the end of the irradiation) needs to be accurately detected to perform imaging in a minimum accumulation time. Therefore, the detection of X-ray irradiation needs to read signals in a wide region of the detecting unit at high speeds.

According to Patent Literature 1, the added neighboring pixel signals are sequentially read. Thus, the signals in a wide region of the detecting unit can be read, but it takes time to read the signals and the X-ray pulse width cannot be accurately detected. Further, according to Patent Literature 2, arbitrarily selected pixel signals are sequentially read. Thus, if the number of selected pixels is small, the amount of X-ray irradiation to the selected pixels is small, whereby it may be difficult to detect the signals. Furthermore, if the number of selected pixels increases, it takes time to read the signals, whereby the X-ray pulse width cannot be accurately monitored.

In view of such problems, the present invention has been made, and an object of the present invention is to provide an imaging apparatus, a control method therefor, and an imaging system capable of more accurately detecting irradiation of X-ray (radiation) and more accurately synchronizing X-ray irradiation with imaging apparatus operations.

Solution to Problem

According to an aspect of the present invention, an imaging apparatus comprising: a detecting unit provided with a plurality of pixels arranged in a matrix, each of the pixels including a conversion element for converting radiation or light into an electric charge and a switch element for outputting an electric signal based on the electric charge; a drive circuit unit for controlling a conducting state of the switching element such that the switching elements at least in one row are turned on together, and a plurality of the switching elements in non-continuous rows are simultaneously at a conducting state; a signal processing unit for adding or averaging the electric signals outputted from the plurality of the switching elements of the non-continuous rows, to generate a detection signal; a comparing unit for comparing the detection signal with a threshold, to determine a start of or an end of an irradiation of the radiation or light; and a control circuit unit for controlling the drive circuit unit or the signal processing unit, based on the determination.

Advantageous Effects of Invention

The present invention can provide an imaging apparatus, a control method therefor, and an imaging system capable of more accurately detecting irradiation of X-ray (radiation) and more accurately synchronizing X-ray irradiation with imaging apparatus operations.

Further features of the present invention will become apparent from the following description of exemplary embodiments with reference to the attached drawings.

BRIEF DESCRIPTION OF DRAWINGS

FIG. 10 is a timing chart illustrating an example of an imaging operation of the imaging apparatus according to the third embodiment of the present invention.

DESCRIPTION OF EMBODIMENTS

Now, with reference to the accompanying drawings, embodiments for carrying out the present invention will be described. Note that the description will be given on an example of X-ray as radiation, but the term "radiation" according to the present invention is not limited to X-ray but includes an electromagnetic wave such as γ radiation and radiation such as α radiation and β radiation.

First Embodiment

Figure 1:
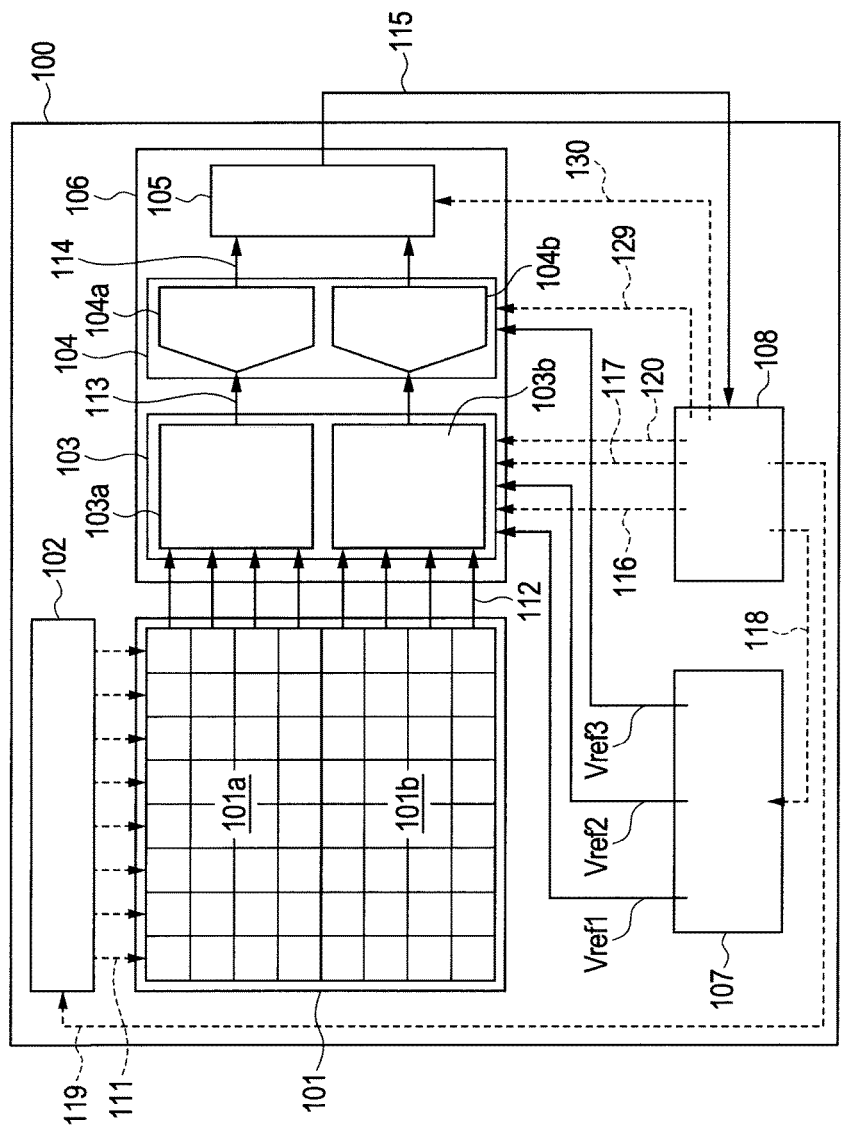
FIG. 1 is a block diagram illustrating an example of an imaging apparatus according to a first embodiment of the present invention.

FIG. 1 is a block diagram illustrating an example of an imaging apparatus according to a first embodiment of the present invention. FIG. 1 illustrates an imaging apparatus 100 which includes a detecting unit 101; a drive circuit unit 102; a signal processing unit 106 including a read-out circuit unit 103, an A/D conversion unit 104, and a digital data processing unit 105; a power supply unit 107, and a control circuit unit 108.

The detecting unit 101 has a plurality of pixels arranged in a matrix for converting radiation or light into an analog electrical signal. The drive circuit unit 102 drives a plurality of pixels of the detecting unit 101 for each row to parallel output analog electrical signals for each row from the plurality of pixels of the detecting unit 101.

For ease of description, the present embodiment assumes that the detecting unit 101 has eight rows by eight columns of pixels, which are divided into two groups: a first pixel group 101a and a second pixel group 101b, each group having four rows of pixels. The pixel signals which are analog electrical signals output from the pixels of the first pixel group 101a are read by a corresponding first read-out circuit unit 103a. Pixel signals 113 which are parallel read from the plurality of pixels and subjected to parallel-serial conversion by the first read-out circuit unit 103a are converted to digital data 114 by a corresponding first A/D conversion unit 104a. Likewise, pixel signals which are analog electrical signals from the second pixel group 101b are read by a corresponding second read-out circuit unit 103b and converted to digital data by a second A/D conversion unit 104b.

The digital data from the first A/D conversion unit 104a and the second A/D conversion unit 104b is input to the digital data processing unit 105, in which signal processing, digital multiplex processing, offset correction, and the like are performed on the digital data to be output as digital image signal (115).

The signal processing unit 106 includes the read-out circuit unit 103 having the first read-out circuit unit 103a and the second read-out circuit unit 103b; the A/D conversion unit 104 having the first A/D conversion unit 104a and the second A/D conversion unit 104b; and the digital data processing unit 105.

The imaging apparatus 100 further includes the power supply unit 107 for supplying the signal processing unit 106 with a bias corresponding to each component unit. More specifically, the power supply unit 107 supplies the read-out circuit unit 103 with reference voltages Vref1 and Vref2; and supplies the A/D conversion unit 104 with a reference voltage Vref3. The imaging apparatus 100 further includes the control circuit unit 108 for controlling at least one of the drive circuit unit 102, the signal processing unit 106, and the power supply unit 107. The control circuit unit 108 supplies the power supply unit 107 with a control signal 118. Further, the control circuit unit 108 supplies the read-out circuit unit 103 with control signals 116, 117, and 120. Furthermore, the control circuit unit 108 supplies the A/D conversion unit 104 with a control signal 129; and supplies the digital data processing unit 105 with a control signal 130. Still furthermore, the control circuit unit 108 supplies the drive circuit unit 102 with a control signal 119. Based on the control signal 119, the drive circuit unit 102 supplies the detecting unit 101 with a drive signal 111.

Figure 2:
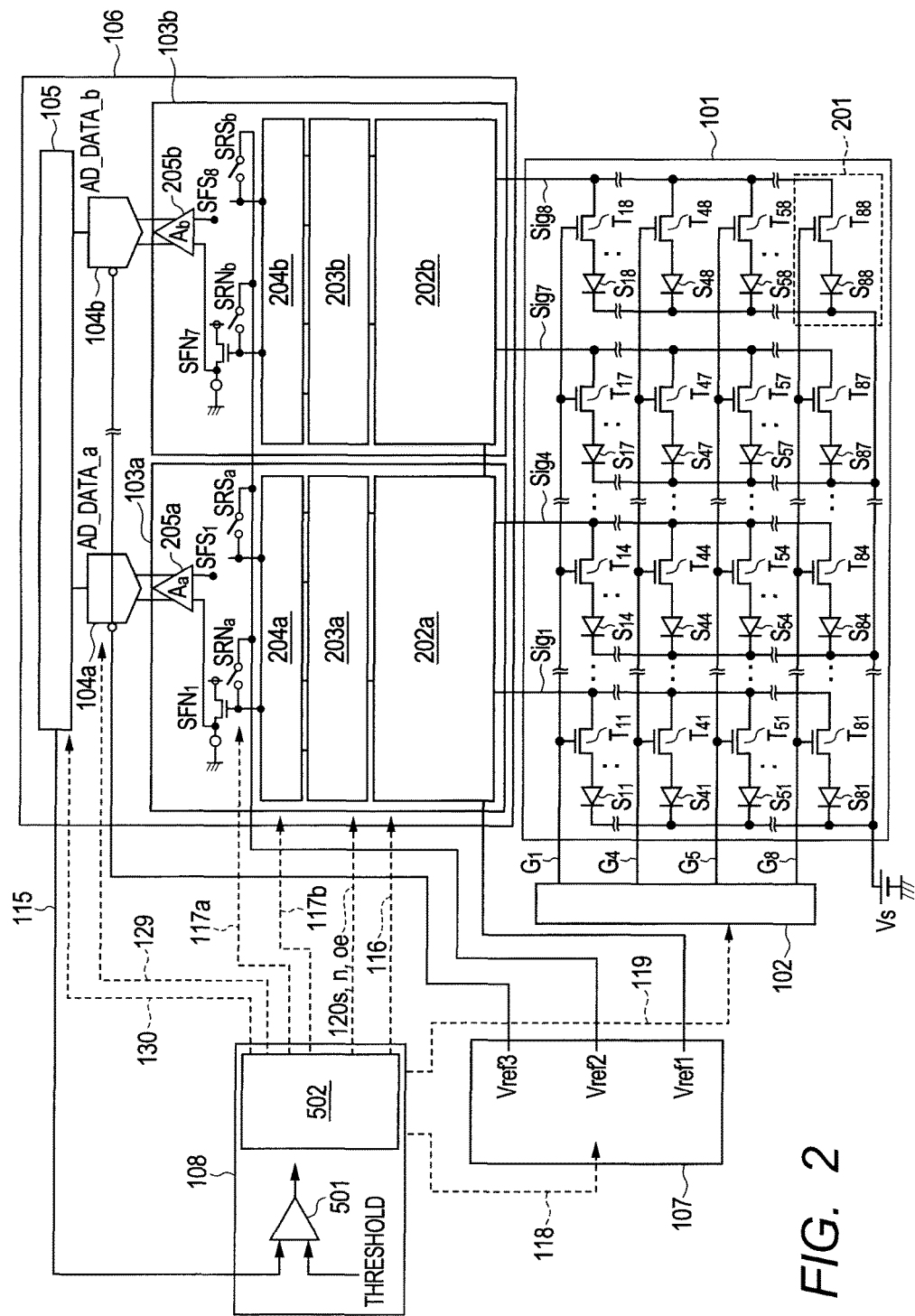
FIG. 2 is a schematic equivalent circuit diagram illustrating an example of the imaging apparatus according to the first embodiment of the present invention.

FIG. 2 is a schematic equivalent circuit diagram illustrating an example of the imaging apparatus according to the first embodiment of the present invention. Note that the same components as described in FIG. 1 are assigned to the same reference numerals or characters in FIG. 2, and the detailed description thereof is omitted.

The detecting unit 101 includes a plurality of pixels 201 arranged in a matrix. FIG. 2 illustrates 8×8 pixels 201 arranged in a matrix of eight rows and eight columns. The pixels 201 include conversion elements S ($S_{11}$ to $S_{88}$), each converting radiation or light to an electric charge; and switch elements T ($T_{11}$ to $T_{88}$), each outputting an electric signal based on the electric charge.

The drive circuit unit 102 can control the conducting states of the switch elements such that the switch elements ($T_{11}$ to $T_{88}$) are in conducting states for each row and the switch elements in non-continuous rows are at least temporarily in conducting states. When a switch element is in a conducting state, the switch element outputs an electrical signal based on the electric charge converted by the conversion element. The operation of the switch element is referred to as an output operation. When a switch element is in a non-conducting state, the switch element accumulates the electric charge in the conversion element. The operation of the switch element is referred to as an accumulating operation.

Suitable examples of the conversion element S for converting light to an electric charge include a photoelectric conversion element such as a PIN photodiode mainly composed of amorphous silicon arranged on an insulating substrate such as a glass substrate. Suitable examples of the conversion element S for converting radiation to an electric charge include an indirect conversion element having a wavelength converter which is provided on a radiation incident side of the above described photoelectric conversion element and converts radiation into light on a wavelength band sensible by the photoelectric conversion element; and a direct conversion element which directly converts radiation to an electric charge.

Suitable examples of the switch element T include a transistor having a control terminal and two main terminals; and a thin-film transistor (TFT) in the case of a pixel in which a photoelectric conversion element is formed on an insulating substrate.

One electrode of the conversion element S is electrically connected to one of the two main terminals (source electrode and drain electrode) of the switch element T; and the other electrode thereof is electrically connected to a bias power supply $V_S$ through a common line.

The control terminals of a plurality of switch elements T of a plurality of pixels in a row direction such as the switch elements $T_{11}$ to $T_{18}$ in the first row are electrically connected commonly to a drive line $G_1$ in the first row. Then, a drive signal for controlling the conducting state and the non-conducting state of the switch element T is supplied by the drive circuit unit 102 for each row through a drive line (such as $G_1$). The drive signal includes a conducting voltage for placing the switch element T in the conducting state; and a non-conducting voltage for placing the switch element T in the non-conducting state.

The other main terminals of switch elements T in a plurality of pixels in a column direction such as the switch elements $T_{11}$ to $T_{81}$ in the first column are electrically connected to a signal line $Sig_1$ in the first column. While the switch element T is in the conducting state, the switch element T outputs an electrical signal based on the electric charge of the conversion element to the read-out circuit unit 103 through the signal line $Sig_1$.

A plurality of signal lines $Sig_1$ to $Sig_8$ arranged in a column direction transfers the electrical signals output from a plurality of pixels of the detecting unit 101 in parallel to the read-out circuit unit 103. According to present embodiment, as illustrated in FIG. 1, the detecting unit 101 is divided into two groups: the first pixel group 101a and the second pixel group 101b, each group having four rows of pixels. The analog electrical signals output from the first pixel group 101a are read in parallel by the corresponding first read-out circuit unit 103a in the read-out circuit unit 103. The analog electrical signals output from the second pixel group 101b are read in parallel by the second read-out circuit unit 103b. At this time, the read-out circuit unit 103 is configured to be able to add or average the electrical signals output by the switch elements included in the pixels 201 in a column direction. Specifically, when the start or the end of radiation irradiation is detected, the signal processing unit 106 is configured to be able to generate detection signals by adding or averaging the electrical signals output by the switch elements included in the pixels 201 in a column direction.

The first read-out circuit unit 103a includes a first amplifier circuit unit 202a for amplifying the electrical signals parallel output from the first pixel group 101a; and a first sampling and holding circuit unit 203a for sampling and holding the electrical signals from the first amplifier circuit unit 202a. The first read-out circuit unit 103a further includes a first multiplexer 204a which sequentially outputs the electrical signals read in parallel from the first sampling and holding circuit unit 203a, as a serial image signal. The first read-out circuit unit 103a further includes a first variable amplifier unit 205a which is an output buffer for performing impedance conversion on the image signals to be output.

Likewise, the second read-out circuit unit 103b includes a second amplifier circuit unit 202b, a second sampling and holding circuit unit 203b, a second multiplexer 204b, and a second variable amplifier unit 205b.

The electrical signals from the pixels are input to the first variable amplifier unit 205a or the second variable amplifier unit 205b through signal buffers SFS. Further, the noise components are input to the first variable amplifier unit 205a or the second variable amplifier unit 205b through noise buffers SFN.

The electrical signals from the pixels input to the first variable amplifier unit 205a from which the noise components are subtracted are input to the first A/D conversion unit 104a. Likewise, the electrical signals from the pixels input to the second variable amplifier unit 205b from which the noise components are subtracted are input to the second A/D conversion unit 104b.

The first A/D conversion unit 104a and the second A/D conversion unit 104b receive a reference voltage Vref3 from the power supply unit 107. Here, a reference voltage Vref2 is input to each gate of the signal buffers SFS of the first read-out circuit unit 103a and the second read-out circuit unit 103b in a predetermined timing from the power supply unit 107 through reset switches SRS.

Further, the reference voltage Vref2 is input to each gate of the noise buffers SFN of the first read-out circuit unit 103a and the second read-out circuit unit 103b in a predetermined timing from the power supply unit 107 through reset switches SRN. In other word, the reset switches SR reset the inputs to the variable amplifier units 205a and 205b in a predetermined timing by supplying each gate of the buffers SF with the reference voltage Vref2 in a predetermined timing.

The control circuit unit 108 controls the imaging apparatus 100. The control circuit unit 108 includes therein a comparing unit 501 that compares a threshold with the detection signal 115 output from the signal processing unit 106 and determines whether or not X-ray (radiation) or light is irradiated. The control circuit unit 108 further includes therein a timing generating unit 502 that controls the imaging apparatus 100 (the drive circuit unit 102, the signal processing unit 106, and the like) based on the result of the comparing unit 501. The control circuit unit 108 (the timing generating unit 502) supplies the first amplifier circuit unit 202a and the second amplifier circuit unit 202b with a control signal 116. The control circuit unit 108 (the timing generating unit 502) supplies the reset switches SRS and SRN with a control signal 117a; and supplies the first multiplexer 204a and the second multiplexer 204b with a control signal 117b. The control circuit unit 108 (the timing generating unit 502) supplies the first sampling and holding circuit unit 203a and the second sampling and holding circuit unit 203b with control signals 120s, 120n, and 120oe. The control circuit unit 108 (the timing generating unit 502) supplies the first A/D conversion unit 104a and the second A/D conversion unit 104b with a control signal 129; and supplies the digital data processing unit 105 with a control signal 130.

Figure 3:
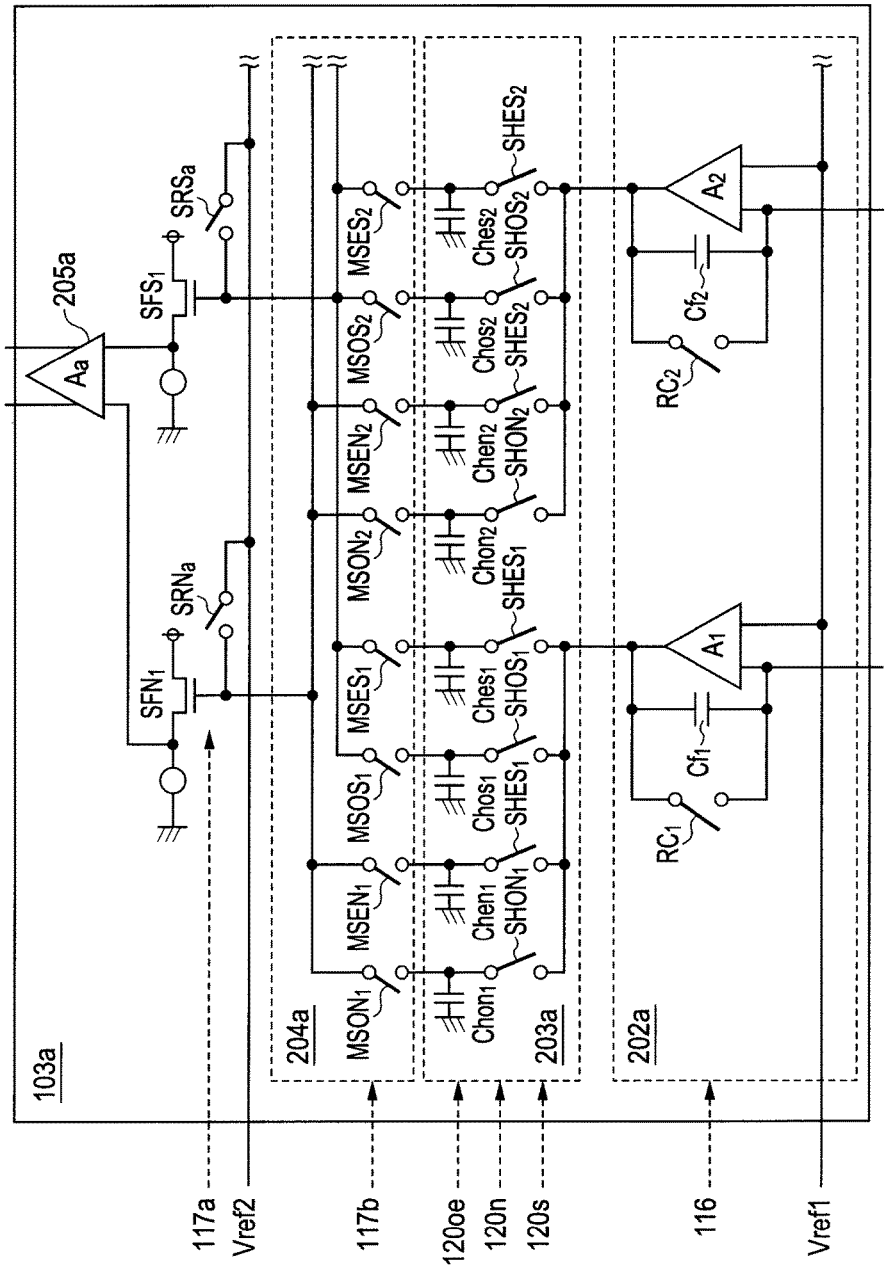
FIG. 3 is an equivalent circuit diagram illustrating an example of details of the read-out circuit unit (first read-out circuit unit) illustrated in FIGS. 1 and 2.

FIG. 3 is an equivalent circuit diagram illustrating an example of details of the read-out circuit unit 103 (first read-out circuit unit 103a) illustrated in FIGS. 1 and 2. The first amplifier circuit unit 202a has an amplifier circuit including an operational amplifier A for amplifying and outputting an electrical signal (pixel signal) read from a pixel according to each signal line; an integrating capacitor Cf; and a reset switch RC for resetting the integrating capacitor Cf. The output electrical signal is input to an inverting input terminal of the operational amplifier A, and the amplified electrical signal is output from an output terminal thereof. The reference voltage Vref1 is input to a non-inverting input terminal of the operational amplifier A from the power supply unit 107. The integrating capacitor Cf is interposed between the inverting input terminal and the output terminal of the operational amplifier A. The reset switch RC is connected in parallel to the integrating capacitor Cf.

The first sampling and holding circuit unit 203a includes an odd row signal sampling and holding circuit, an even row signal sampling and holding circuit, an odd row noise sampling and holding circuit, and even row noise sampling and holding circuit corresponding to each amplifier circuit.

The odd row signal sampling and holding circuit includes a sampling switch SHOS for sampling an electrical signal from an odd row pixel; and a sampling capacitor Chos for holding an odd row pixel signal. The even row signal sampling and holding circuit includes a sampling switch SHES for sampling an even row pixel signal; and a sampling capacitor Ches for holding an even row pixel signal. The odd row noise sampling and holding circuit includes a sampling switch SHON for sampling a noise component of the operational amplifier A before sampling the odd row pixel signal; and a sampling capacitor Chon for holding the noise signal. The even row noise sampling and holding circuit includes a sampling switch SHEN for sampling noise of the operational amplifier A before sampling the even row pixel signal; and a sampling capacitor Chen for holding the noise signal.

The first multiplexer 204a includes a switch MSOS corresponding to the odd row signal sampling and holding circuit; and a switch MSES corresponding to the even row signal sampling and holding circuit, which are provided for each amplifier circuit. The first multiplexer 204a further includes a switch MSON corresponding to the odd row noise sampling and holding circuit; and a switch MSEN corresponding to the even row noise sampling and holding circuit, which are provided for each amplifier circuit. Then, each switch is sequentially selected, whereby the parallel signal of the pixel signal or the noise component is converted to the serial signal.

Figure 4:
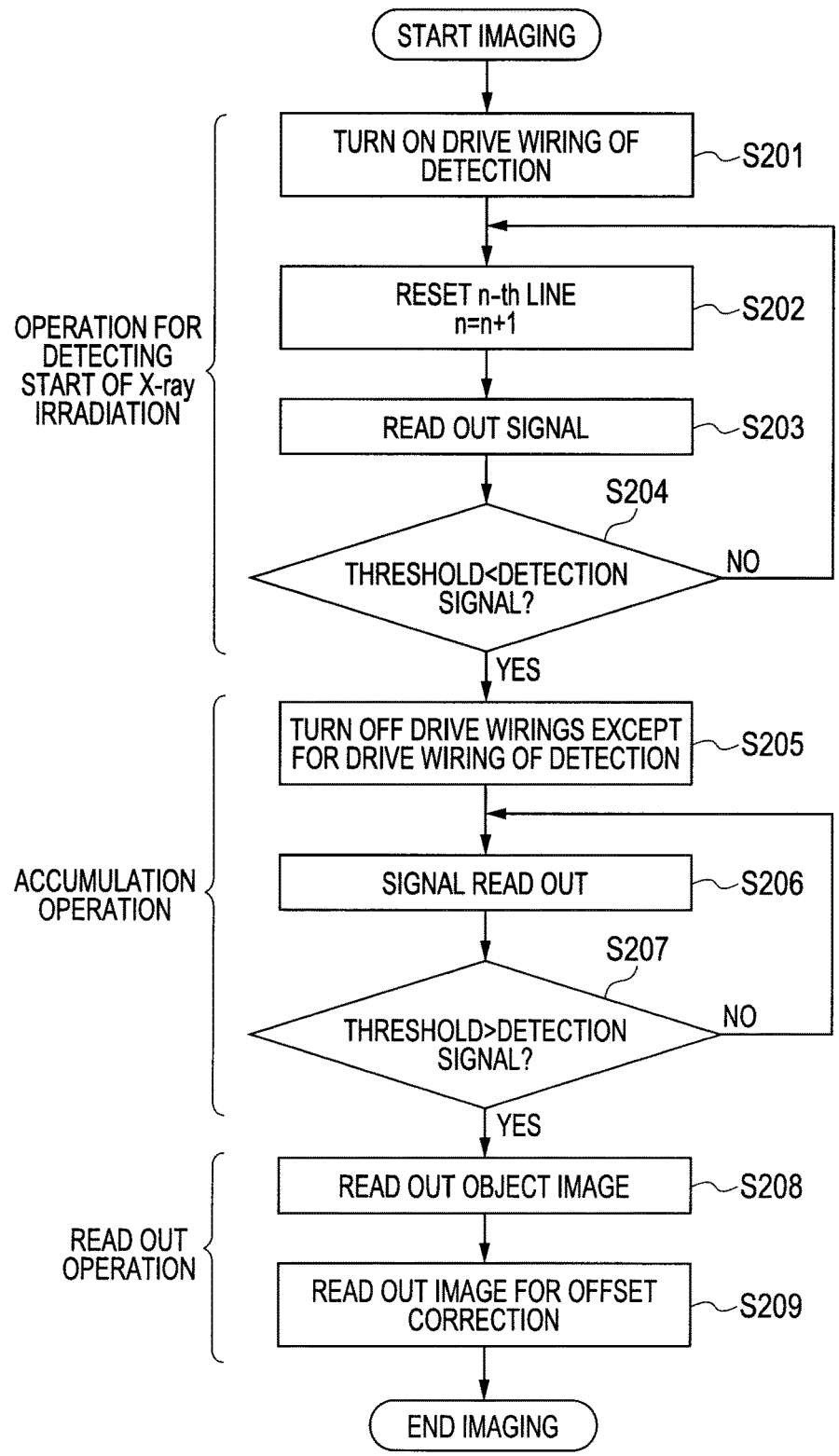
FIG. 4 is a flowchart illustrating an example of a processing procedure by a control method of the imaging apparatus according to the first embodiment of the present invention.
Figure 5:
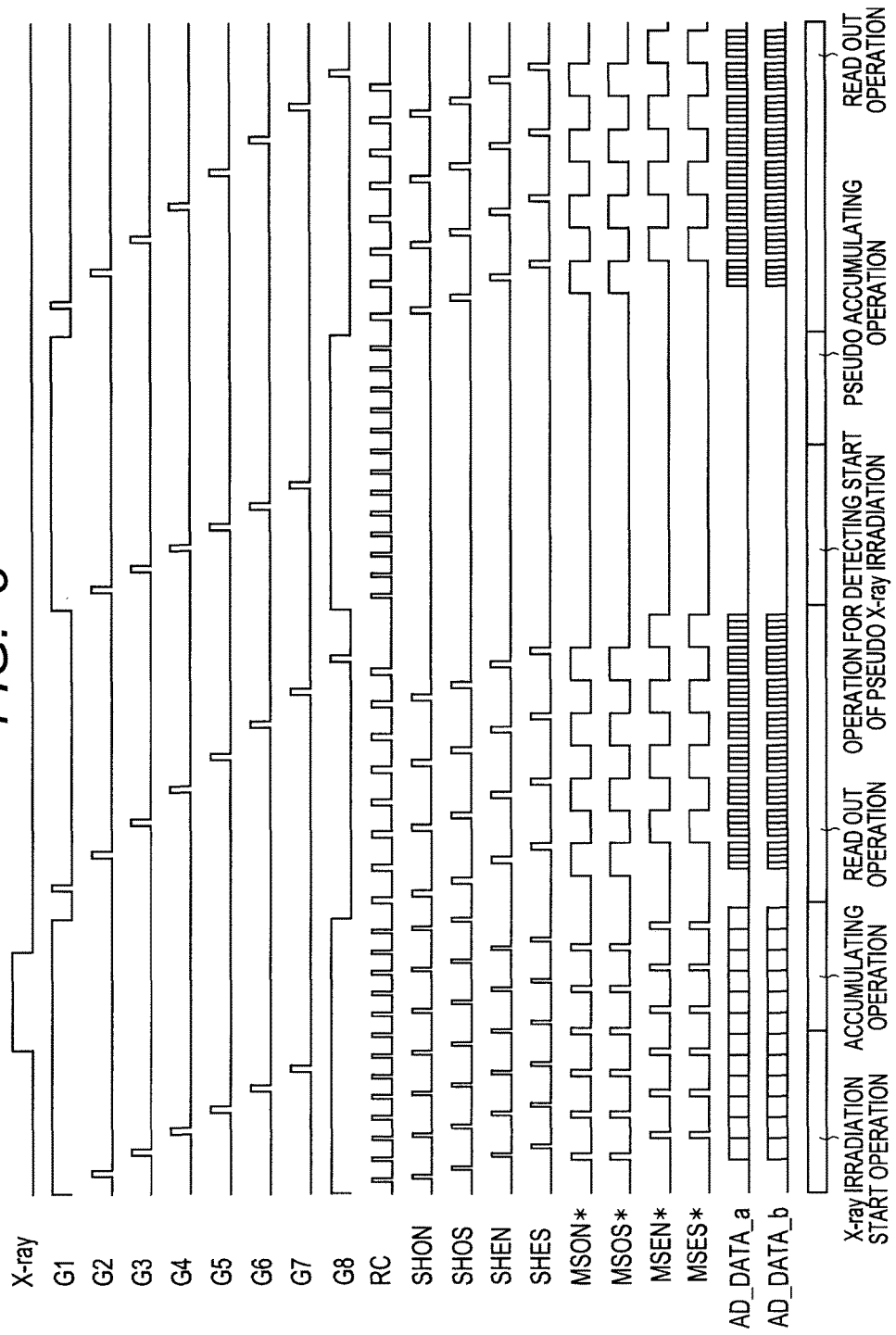
FIG. 5 is a timing chart illustrating an example of an imaging operation of the imaging apparatus according to the first embodiment of the present invention.
Figure 6:
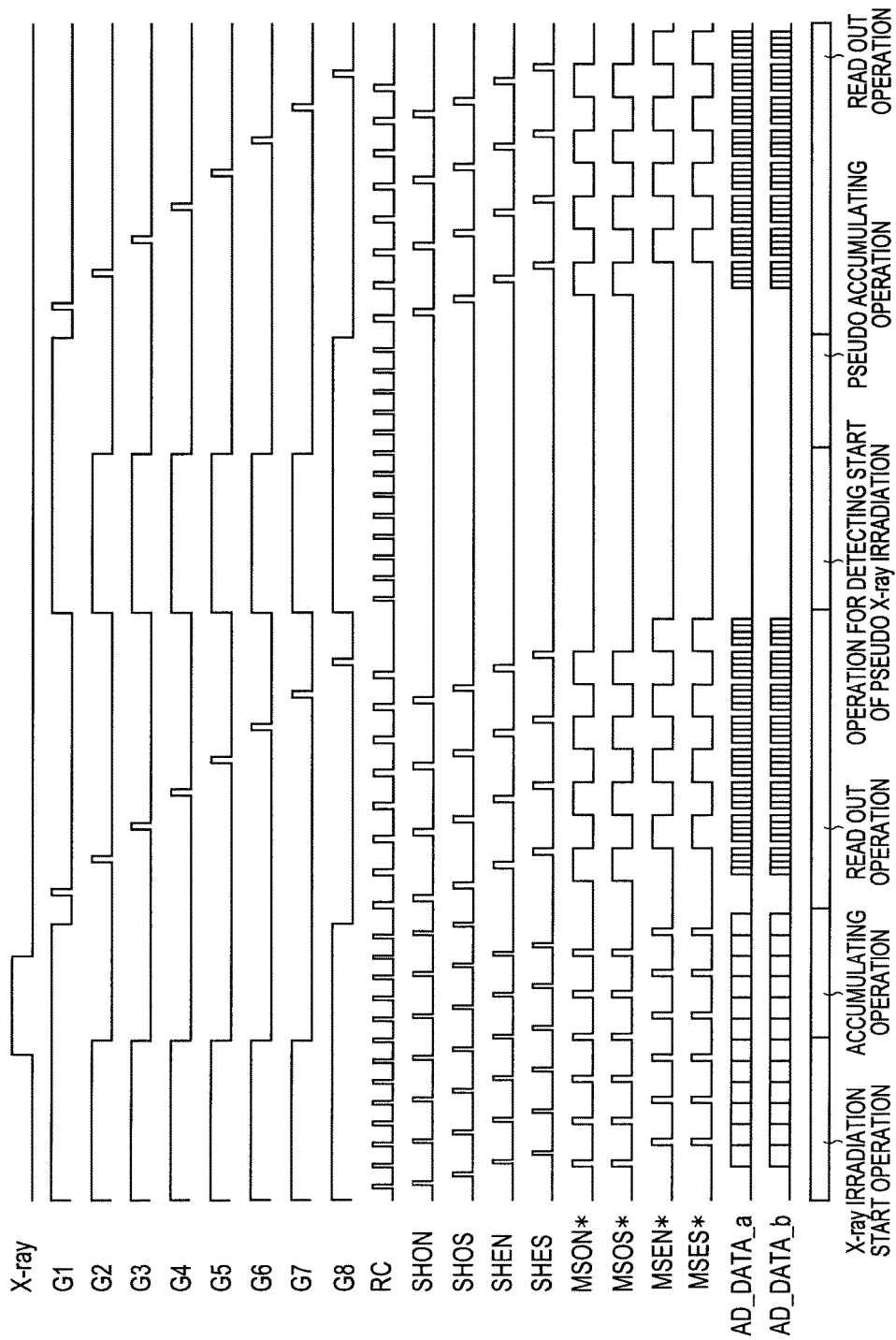
FIG. 6 is a timing chart illustrating another example of the imaging operation of the imaging apparatus according to the first embodiment of the present invention.

Now, with reference to FIGS. 4, 5, and 6, the operation of the imaging apparatus of the present invention will be described. FIG. 4 is a flowchart illustrating an example of a processing procedure by a control method of the imaging apparatus according to the first embodiment of the present invention. Note that the process of each step in the flowchart illustrated in FIG. 4 is performed, for example, under the control of the control circuit unit 108. FIGS. 5 and 6 each are timing charts illustrating examples of an imaging operation of the imaging apparatus according to the first embodiment of the present invention.

Here, the description starts with the operation of detecting the start of X-ray irradiated in a pulse shape (hereinafter referred to as an X-ray irradiation start detection operation). Note that the present embodiment will focus on the operation of detecting the start of X-ray irradiation, but this is just an example. For example, the present embodiment can be applied to the operation of detecting the start of light.

First, in order to detect the start of X-ray irradiation, under the control of the control circuit unit 108, the drive circuit unit 102 drives switch elements in at least non-continuous rows, here, two rows in the first and eighth rows: switch elements $T_{11}$ to $T_{18}$ and $T_{81}$ to $T_{88}$ such that the two rows are simultaneously in conducting states. This operation corresponds to step S201 "detection drive line ON" in FIG. 4. Then, the imaging apparatus detects X-ray irradiated to the conversion elements $S_{11}$ to $S_{18}$ and $S_{81}$ to $S_{88}$. Here, the switch elements included in the pixels in non-continuous rows are placed in conducting states and the pixels in the non-continuous rows are located in the outermost row of the detecting unit 101. Note that under the control of the control circuit unit 108, the drive circuit unit 102 can change the rows of the pixels including the switch elements to be placed in conducting states in the detection output operation. For example, under the control of the control circuit unit 108, in response to user input, the drive circuit unit 102 can change the rows of the pixels including the switch elements to be placed in conducting states in the detection output operation. For example, under the control of the control circuit unit 108, according to the object portion to be imaged, the drive circuit unit 102 can change the rows of the pixels including the switch elements to be placed in conducting states in the detection output operation.

In a state in which the switch elements $T_{11}$ to $T_{18}$ and $T_{11}$ to $T_{88}$ are placed in conducting states, the control signal 116 is supplied from the control circuit unit 108, the integrating capacitor Cf is reset by the reset switch RC, and the amplifier circuit is reset.

Then, the control circuit unit 108 supplies the sampling and holding circuit units 203a and 203b with the control signals 120n and 120oe. Then, the sampling switch SHON of the odd row noise sampling and holding circuit is made conducting, and the noise component of the amplifier circuit is transferred from the reset amplifier circuit to the sampling capacitor Chon. Then, the sampling switch SHON is made non-conducting and the noise component is held by the sampling capacitor Chon.

Then, the conversion elements not monitoring X-ray are also reset to reset dark current by placing the switch elements other than the two rows of switch elements $T_{11}$ to $T_{18}$ and $T_{81}$ to $T_{88}$ in conducting states in steps S202 and S203 in FIG. 4. During this time, the switch elements $T_{11}$ to $T_{18}$ and $T_{81}$ to $T_{88}$ continue to maintain the conducting states and detect the start of X-ray irradiation. Here, the dark current reset operation may be such that as illustrated by the timing chart in FIG. 6, some or all lines continue to be turned on and when the start of X-ray irradiation is confirmed, the lines are turned off; alternatively as illustrated by the timing chart in FIG. 5, the lines G2 to G7 are sequentially turned on and off to reset.

When a certain time has elapsed since the sampling switch SHON was non-conducting, the control circuit unit 108 supplies the sampling and holding circuit units 203a and 203b with control signals 120s and 120oe. Then, the sampling switch SHOS of the odd row signal sampling and holding circuit is made conducting, the signal is transferred to the sampling capacitor Chos, and then the sampling switch SHOS is made non-conducting.

When the X-ray generating apparatus (radiation generating apparatus) irradiates the conversion element $S_{11}$ to $S_{18}$ and $S_{81}$ to $S_{88}$ of the detecting unit 101 with X-ray, each conversion element S generates an electric charge based on the irradiated X-ray. Here, the generated electric charge is transferred to the integrating capacitor Cf of the amplifier circuit, and a difference between when the sampling switch SHON is made non-conducting and when the sampling switch SHOS is made non-conducting appears as a pixel signal which is an electrical signal.

Then, the imaging apparatus 100 performs the following signal processing. The control circuit unit 108 supplies the reset switches SRS and SRN with the control signal 117a. Then, the reset switches SRS and SRN are made conducting, the reference voltage Vref2 is supplied to each gate of the buffers SFS and SFN, and each input to the variable amplifier units 205a and 205b is reset.

Then, the reset switches SRS and SRN are made non-conducting and the control circuit unit 108 supplies the multiplexers 204a and 204b with the control signal 117b. Accordingly, the switch MSOS1 and the switch MSON1 of the first multiplexer 204a are made conducting. Then, the pixel signal of the first column pixel is input to the first variable amplifier unit 205a through the buffer SFS, and the noise component is input thereto through the buffer SFN. The switch MSOS5 and switch MSON5 of the second multiplexer 204b are made conducting at the same time. Accordingly, the pixel signal of the fifth column pixel to which the noise component is added is input to the second variable amplifier unit 205b through the buffer SFS, and the noise component is input thereto through the buffer SFN.

The variable amplifier units 205a and 205b each perform differential processing on the noise component and the pixel signal to which the noise component is added. Then, the pixel signal subjected to differential processing is amplified and output from the variable amplifier units 205a and 205b. Accordingly, the noise component of each amplifier circuit is removed from the output from the amplifier circuit. The A/D conversion units 104a and 104b convert each output pixel signal to digital data AD_DATA_a and AD_DATA_b respectively and output the digital data to the digital data processing unit 105.

Then, a pixel data output operation is performed on the second and sixth column pixels. Then, the A/D conversion units 104a and 104b output digital data AD_DATA_a and AD_DATA_b respectively to the digital data processing unit 105. Likewise, a pixel data output operation is sequentially performed on the third to fourth and seventh to eighth column pixels.

According to the aforementioned example, the switch MSOS 1 to 4 and the switch MSON 1 to 4 are sequentially switched to convert to the signals to digital data. Alternatively, four switches are simultaneously turned on and the added and averaged signals are collectively converted once to digital data, whereby it is also possible to increase the speed of detecting the start of irradiation of X-ray (radiation) or light. According to the aforementioned example, two read-out circuit units 103: the read-out circuit units 103a and 103b are operated, but only one of the read-out circuit units may be operated, whereby the detection can be performed with minimum power consumption. Further, the Cf capacitance of the read-out circuit unit 103 may be increased at detection than when the object image is read so as to increase and read the signal for detection as described later. Furthermore, in order to increase the read speed, it is also possible to reduce the time constant of a filter inside the read-out circuit unit 103.

The signal converted to digital data is input to the digital data processing unit 105, in which the sum, an averaged value, a maximum value, or a minimum value of AD_DATA_a and AD_DATA_b is calculated (generated) as the detection signal 115. Then, the control circuit unit 108 inputs the detection signal 115 to the comparing unit 501. Then, the comparing unit 501 compares the detection signal 115 with a threshold to determine whether or not X-ray is irradiated. This operation corresponds to step S204 in FIG. 4. Here, for determination of an X-ray start pulse, if the detection signal 115 input to the comparing unit 501 is greater than a preset threshold, a determination is made that X-ray irradiation is started.

A noise level is measured in advance and the threshold is set to a value sufficiently large for the noise level. Alternatively, a differential value from the previous monitor results may be calculated and evaluated by the amount of increase.

According to the present embodiment, the comparing unit 501 is included in the control circuit unit 108, but for example, the comparing unit 501 may be included in the digital data processing unit 105 to perform comparison determination. If a comparison determination is made that X-ray irradiation is not started (NO in step S204 in FIG. 4), the process returns to step S202 in FIG. 4, in which "detection drive line ON" continues to be performed. If a comparison determination is made that X-ray irradiation is started (YES in step S204 in FIG. 4), the process moves to the accumulating operation.

The accumulating operation starts with "drive line other than detection drive line OFF" in step S205 in FIG. 4, in which the switch elements other than the two rows: switch elements $T_{11}$ to $T_{18}$ and $T_{81}$ to $T_{88}$ are placed in the non-conducting states. Then, like the X-ray irradiation start detection operation, in "read signal" in step S206 in FIG. 4, the read-out circuit units 103a and 103b are operated.

In the digital data processing unit 105, the sum, an averaged value, a maximum value, or a minimum value of the input AD_DATA_a and AD_DATA_b is calculated (generated) as the detection signal 115. Then, the control circuit unit 108 inputs the detection signal 115 to the comparing unit 501, which compares the detection signal 115 with the threshold ("threshold> detection signal?" in step S207 in FIG. 4) to determine whether or not X-ray is irradiated. For X-ray irradiation end detection, if the detection signal 115 is less than a preset threshold, a determination is made that X-ray irradiation is ended. Note that the threshold at this time may be replaced with a threshold at X-ray irradiation start detection operation. Note also that the switch elements other than the two rows of the switch elements $T_{11}$ to $T_{18}$ and $T_{81}$ to $T_{88}$ are turned off. Thus, based on the irradiated X-ray, each conversion element generates an electric charge and each conversion element accumulates the electric charge.

If the X-ray irradiation end is confirmed (YES in step S207 in FIG. 4), the process moves to the read operation. If the X-ray irradiation end is not confirmed (NO in step S207 in FIG. 4), the process returns to step S206 in FIG. 4.

The read operation starts with "read object image" in step S208 in FIG. 4, in which the control circuit unit 108 supplies the read-out circuit units 103a and 103b, and the drive circuit unit 102 with a control signal. Then the drive circuit unit 102 places the switch elements in non-continuous rows in the non-conducting state. Further, the drive circuit unit 102 sequentially supplies the drive lines from the first row drive line $G_1$ to the drive line $G_8$ with a conducting voltage to read the electric charge accumulated in the conversion element.

First, the control circuit unit 108 supplies the amplifier circuit unit 202 with the control signal 116, and the reset switch RC resets the integrating capacitor Cf to reset the amplifier circuit. Then, the control circuit unit 108 supplies the sampling and holding circuit unit 203 with the control signals 120n and 120oe. Then, the sampling switch SHON of the odd row noise sampling and holding circuit is made conducting, and the noise component of the amplifier circuit is transferred from the reset amplifier circuit to the sampling capacitor Chon. Subsequently, the sampling switch SHON is made non-conducting and the noise component is held by the sampling capacitor Chon.

Then, the control circuit unit 108 supplies the drive circuit unit 102 with the control signal 119. Based on the control signal 119, the drive circuit unit 102 outputs a conducting voltage to the first row drive line $G_1$ to place the switch elements $T_{11}$ to $T_{18}$ in the conducting state. When the switch elements $T_{11}$ to $T_{18}$ are in the conducting state, the electrical signals accumulated in the conversion elements $S_{11}$ to $S_{18}$ and based on the electric charge are output to the integrating capacitor Cf. Then, an output proportional to the electrical signal output from the amplifier circuit appears. When the electrical signals are fully output, the switch elements $T_{11}$ to $T_{18}$ are placed in the non-conducting state.

Then, the control circuit unit 108 supplies the sampling and holding circuit unit 203 with the control signals 120s and 120oe. Accordingly, the sampling switch SHOS of the odd row signal sampling and holding circuit is made conducting, and the signal is transferred to the sampling capacitor Chos. Subsequently, the sampling switch SHOS is made non-conducting, and the pixel signal based on the irradiated X-ray is stored in the sampling capacitor Chos.

Then, the control circuit unit 108 supplies the reset switches SRS and SRN with the control signal 117a. Accordingly, the reset switches SRS and SRN are made conducting, and the reference voltage Vref2 is supplied to each gate of the buffers SFS and SFN to reset the input to the variable amplifier units 205a and 205b.

Then, the reset switches SRS and SRN are made non-conducting, and the control circuit unit 108 supplies each multiplexer with the control signal 117b. Accordingly, the switch MSOS1 and the switch MSON1 of the first multiplexer 204a is made conducting. Accordingly, the pixel signal of the first column pixel is input to the first variable amplifier unit 205a through the buffer SFS, and the noise component is input thereto through the buffer SFN. The switch MSOS5 and switch MSON5 of the second multiplexer 204b are made conducting at the same time. Accordingly, the pixel signal of the fifth column pixel to which the noise component is added is input to the second variable amplifier unit 205b through the buffer SFS, and the noise component is input thereto through the buffer SFN.

Each variable amplifier performs differential processing on the noise component and the pixel signal to which the noise component is added. Then, the pixel signal subjected to differential processing is amplified and output from the variable amplifier. Accordingly, the noise component of each amplifier circuit is removed from the output from the amplifier circuit. The A/D conversion units 104a and 104b convert each output pixel signal to digital data S (1, 1) and S (1, 5) respectively and output the digital data to the digital data processing unit 105.

Then, the pixel data output operation is performed on the second and sixth column pixels. Then, the A/D conversion units 104a and 104b output the digital data S (1, 2) and S (1, 6) respectively to the digital data processing unit 105. Likewise, the pixel data output operation is sequentially performed on the third to fourth and seventh to eighth column pixels. Likewise, the pixel data output operation is performed on the second to eighth row pixels, whereby an X-ray irradiated object image can be acquired.

Further, in the operation: "read offset correction image" in step S209 in FIG. 4 and illustrated by the timing chart in FIG. 5, an offset image without X-ray irradiation is acquired. Therefore, after the read operation following the X-ray irradiation, the X-ray irradiation start detection operation, the accumulating operation, and the read operation are repeated once more in the same amount of time in a state without X-ray irradiation to acquire the offset image. Then, the digital data processing unit 105 performs subtraction processing on the object image and the offset image for offset correction.

In order to detect the start or the end of X-ray irradiation, the present embodiment uses the first row switch elements $T_{11}$ to $T_{18}$ and the eighth row switch elements $T_{81}$ to $T_{88}$ as the switch elements in non-continuous rows, but when the same row elements continue to be used for monitoring, the conversion element S or the switch element T may be deteriorated. Accordingly, the first row switch elements $T_{11}$ to $T_{18}$ and the second row switch elements $T_{21}$ to $T_{28}$; and the eighth row switch elements $T_{81}$ to $T_{88}$ and the seventh row switch elements $T_{71}$ to $T_{78}$ may be alternately used to prevent deterioration.

According to the present embodiment, the pixels detecting two rows of X-ray including the switch elements $T_{11}$ to $T_{18}$ and $T_{81}$ to $T_{88}$ do not perform the accumulating operation, and thus at read operation, the row pixels have no X-ray information and no signal. Therefore, the rows can be treated as peripheral dummy rows not used by the user or as defect row pixels to perform defect correction using adjacent row pixels for interpolation. Here, the defect correction is performed, for example, by the digital data processing unit 105. The digital data processing unit 105 performing the defect correction constitutes "correcting unit". When a row is used as the defect row and the rows adjacent (upper and lower) to the row do the accumulating operation, correction can be made using the pixel signals (electrical signals) of the upper and lower row pixels, whereby correction accuracy can be increased. Thus, when X-ray is detected, a wide range of X-ray can be detected at high speeds by detection in non-adjacent discontinuous rows, the start or the end of X-ray irradiation can be detected with good precision, and high-precision defect correction can be performed.

Before starting X-ray imaging, a radiologist selects the portion to be imaged and determines the conditions for the X-ray generating apparatus based on the selected portion. Accordingly, in conjunction with the portion to be imaged, the X-ray detecting rows are arranged in a region having a large amount of X-ray transmission, whereby the detection precision of the detecting unit 101 can be increased. For example, when the chest is imaged, the regions such as an armpit or a neck side of the object in which X-ray is directly input to the imaging apparatus 100 without transmitting through the object are easy to detect the start or the end of X-ray irradiation. In a case in which imaging is performed without selecting a portion to be imaged, a radiologist can arbitrarily select the rows for use in detection. Then, for example, the control circuit unit 108 detects the selected rows and controls the drive circuit unit 102 to detect the start or the end of X-ray irradiation.

Second Embodiment

Now, with reference to FIGS. 7 and 8, a second embodiment of the present invention will be described. The second embodiment is different from the first embodiment in the configuration of the imaging apparatus. Note that detailed description of the same apparatus configuration and operation as those of the first embodiment will be omitted.

Figure 7:
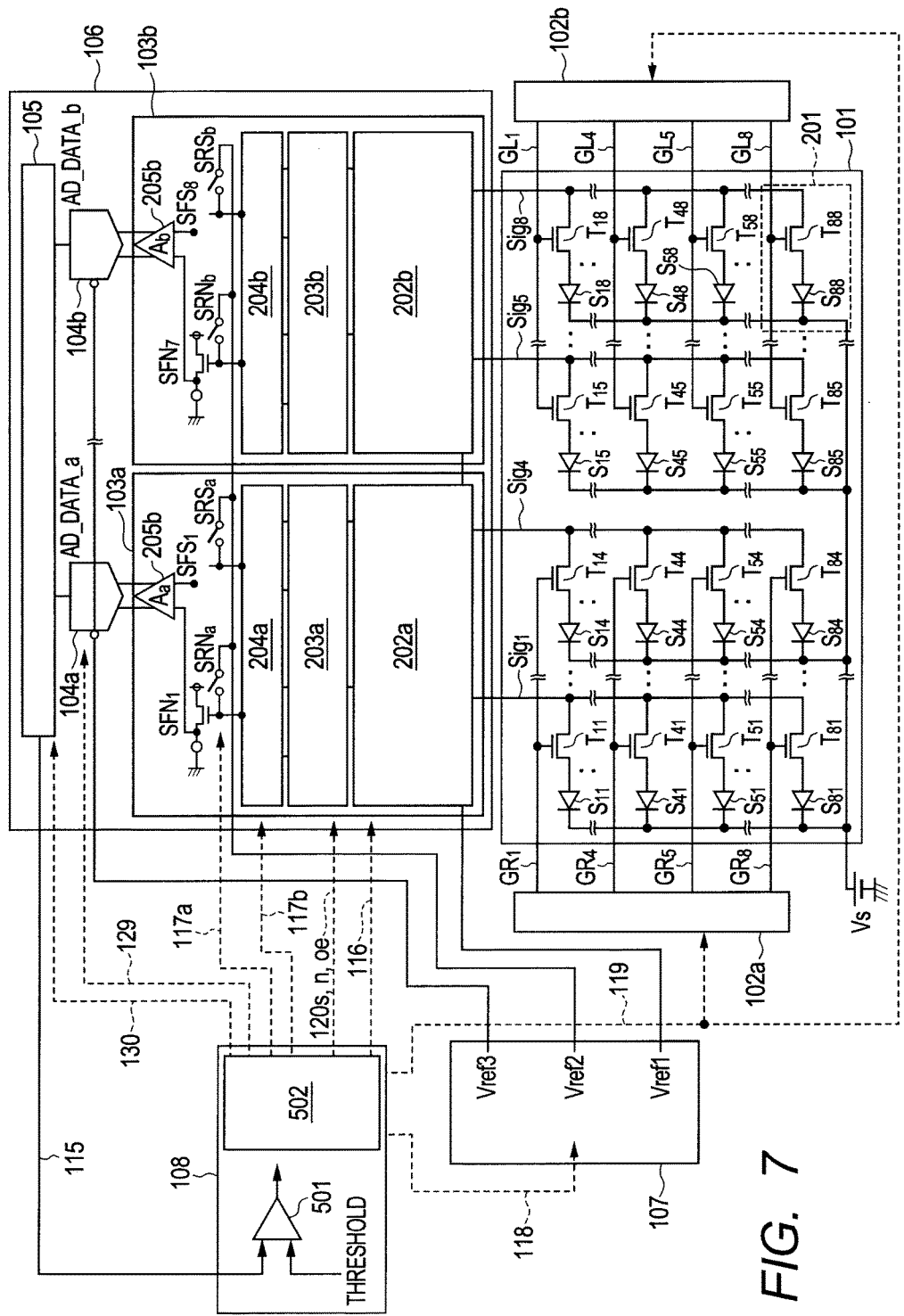
FIG. 7 is an equivalent circuit diagram illustrating an example of an imaging apparatus according to a second embodiment of the present invention.
Figure 8:
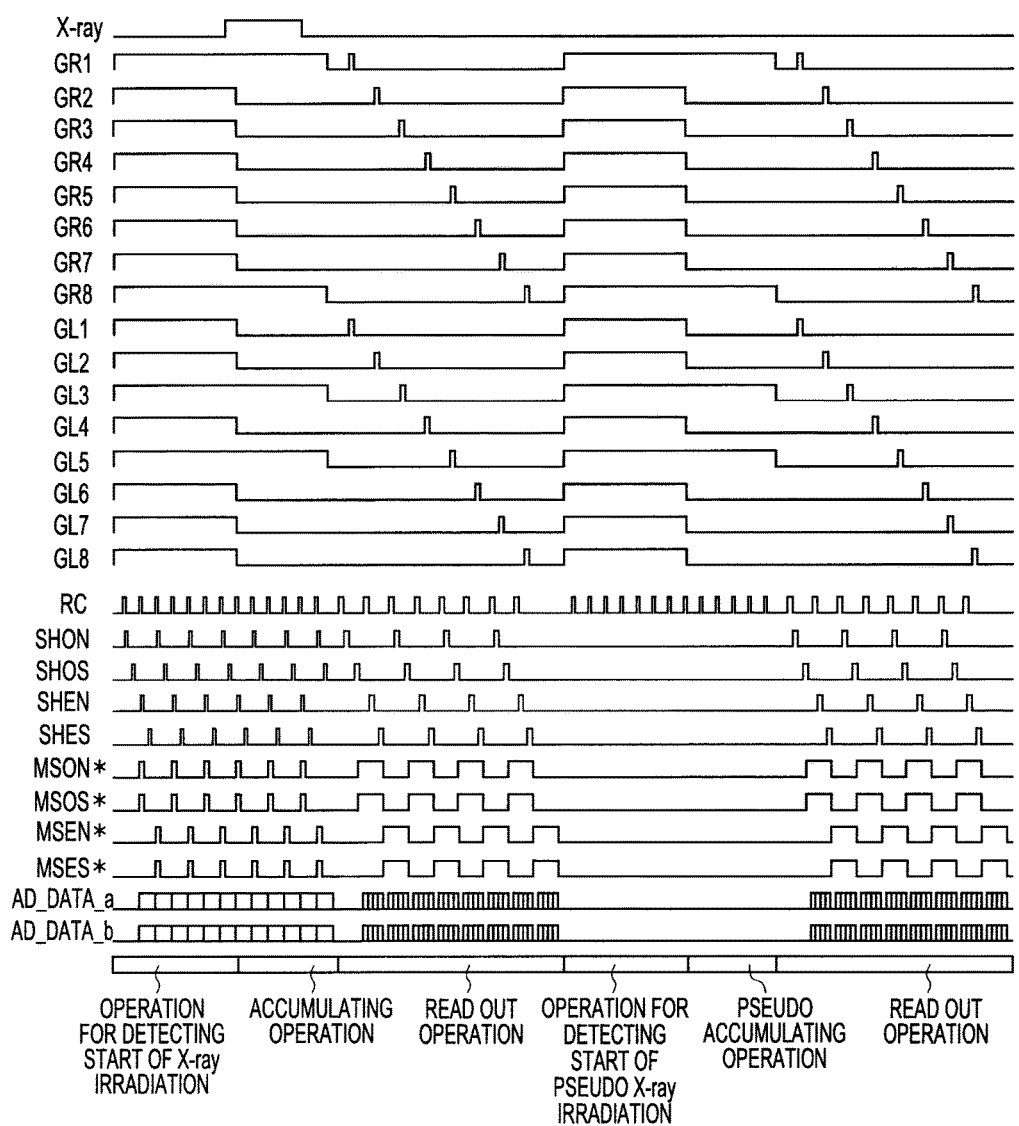
FIG. 8 is a timing chart illustrating an example of an imaging operation of the imaging apparatus according to the second embodiment of the present invention.

FIG. 7 is an equivalent circuit diagram illustrating an example of the imaging apparatus according to the second embodiment of the present invention. FIG. 8 is a timing chart illustrating an example of an imaging operation of the imaging apparatus according to the second embodiment of the present invention.

In the first embodiment, the drive lines $G_1$ to $G_8$ are common in a row direction, but in the second embodiment, the drive lines are divided at the center of the detecting unit 101. More specifically, a plurality of row pixels of the detecting unit 101 is divided into a plurality of groups (two groups in the example of FIG. 7). The drive line $GR_1$ to $GR_8$ are configured to receive a drive signal from the drive circuit unit 102a and the drive line $GL_1$ to $GL_8$ are configured to receive a drive signal from the drive circuit unit 102b.

Thus, in the X-ray irradiation start detection operation and the accumulating operation, the drive line $GR_1$ is controlled to turn the switch elements $T_{11}$ to $T_{14}$ on and the drive line $GR_8$ is controlled to turn the switch elements $T_{81}$ to $T_{84}$ on. Further, the drive line $GL_3$ is controlled to turn the switch elements $T_{35}$ to $T_{38}$ on and the drive line $GL_5$ is controlled to turn the switch elements $T_{55}$ to $T_{58}$ on. Thereby, the start or the end of an X-ray pulse is detected. Thus, the pixel positions for detecting X-ray irradiation can be dispersed, whereby the detection rate of detecting the start or the end of X-ray irradiation can be higher than that of the first embodiment.

Third Embodiment

Figure 9:
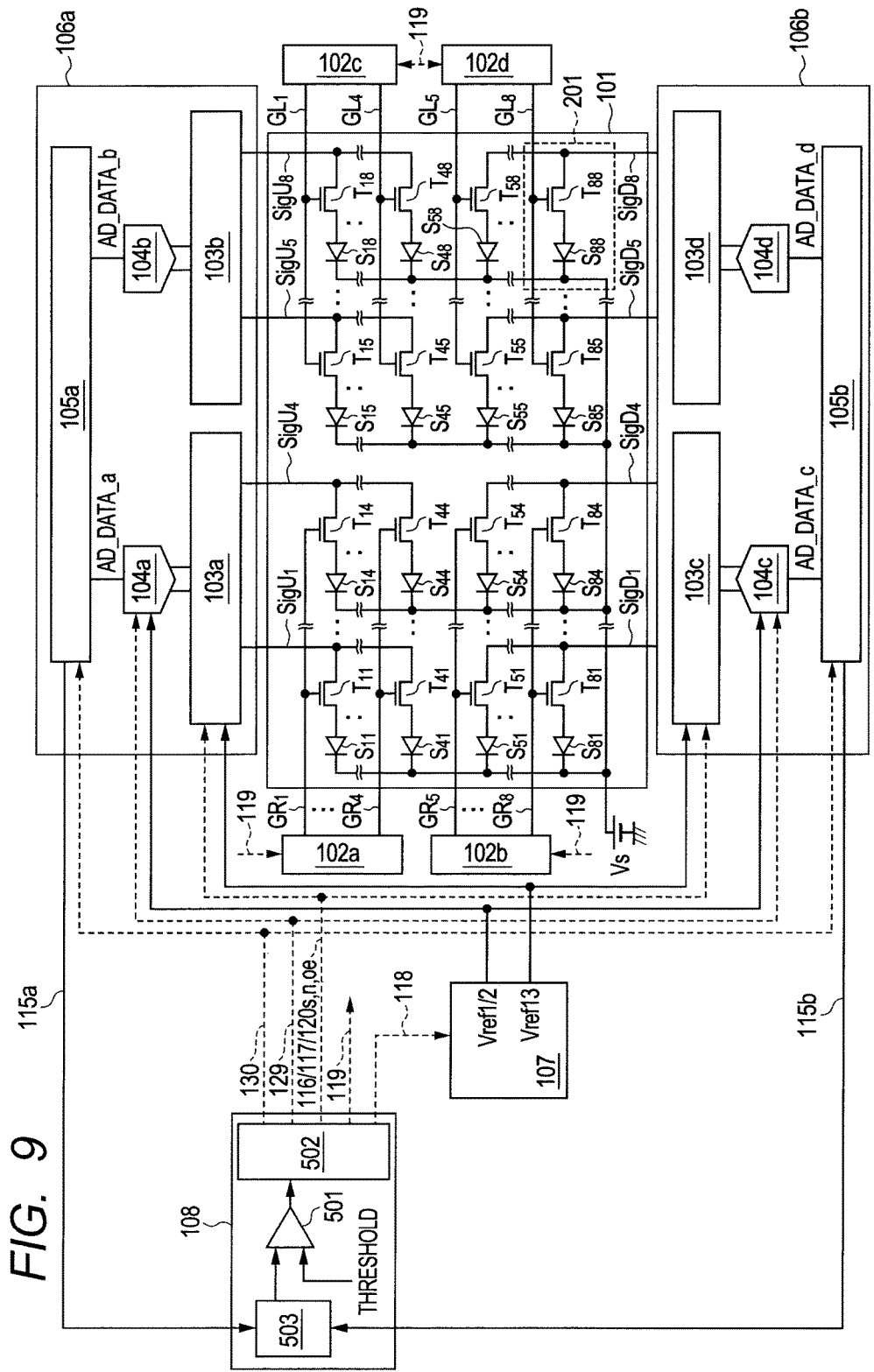
FIG. 9 is an equivalent circuit diagram illustrating an example of an imaging apparatus according to a third embodiment of the present invention.

With reference to FIGS. 9 and 10, a third embodiment of the present invention will be described. The third embodiment is different from the first and second embodiments in the configuration of the imaging apparatus. Note that detailed description of the same apparatus configuration and operation as those of the first and second embodiments will be omitted.

FIG. 9 is an equivalent circuit diagram illustrating an example of the imaging apparatus according to the third embodiment of the present invention. FIG. 10 is a timing chart illustrating an example of an imaging operation of the imaging apparatus according to the third embodiment of the present invention.

In the first and second embodiments, the signal lines $Sig_1$ to $Sig_8$ are common in a column direction, but in the third embodiment, the signal lines are divided at the center of the detecting unit 101. The signal lines $SigU_1$ to $SigU_4$ are connected to the read-out circuit unit 103a, and the signal lines $SigU_5$ to $SigU_8$ are connected to the read-out circuit unit 103b. The signal lines $SigD_1$ to $SigD_4$ are connected to the read-out circuit unit 103c, and the signal lines $SigD_5$ to $SigD_8$ are connected to the read-out circuit unit 103d.

Thus, in the X-ray irradiation start detection operation and the accumulating operation, the drive line $GR_1$ is controlled to turn the switch elements $T_{11}$ to $T_{14}$ on, and the drive line $GR_8$ is controlled to turn the switch elements $T_{81}$ to $T_{84}$ on. Further, the drive line $GL_3$ is controlled to turn the switch elements $T_{35}$ to $T_{38}$ on, and the drive line $GL_5$ is controlled to turn the switch elements $T_{55}$ to $T_{58}$ on. Thereby, the start or the end of X-ray irradiation is detected.

In the first and second embodiments, two rows of signal electric charges at X-ray monitoring are added to the integrating capacitor Cf of the read-out circuit unit 103. On the contrary, in the present embodiment, an adder 503 in the control circuit unit 108 adds two rows of signal electric charges and then the comparing unit 501 determines whether X-ray irradiation is started or ended.

In the case of moving image radiographing, the frame rate can be increased by dividing the signal lines Sig at the center to increase the speed of read operation. Thus, in the detection of X-ray irradiation during the X-ray irradiation start detection operation and the accumulating operation, the signals read by the read-out circuit units 103a to 103d are converted to digital data by the A/D conversion units 104a to 104d and added by the adder 503, whereby an X-ray pulse can be monitored.

Application Example

Figures 11A, 11B:
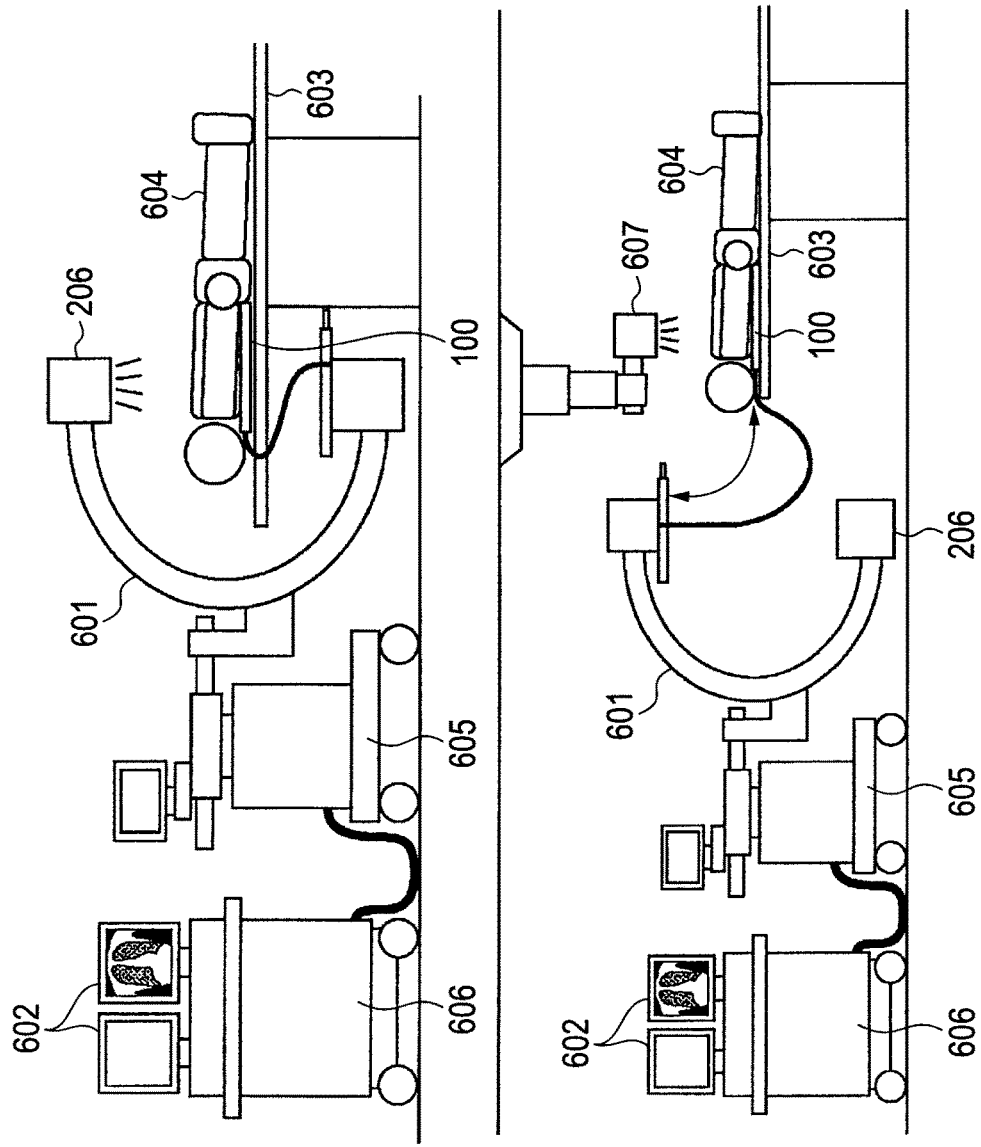
FIGS. 11A and 11B illustrate an example of application of the present invention and are schematic configuration drawings of a radiation imaging system using a portable radiation imaging apparatus capable of fluoroscopic radiographing and still image radiographing.

FIGS. 11A and 11B each illustrate an example of application of the present invention to a portable radiation imaging apparatus. FIG. 11A illustrates an example of application of the present invention and is a schematic configuration drawing of a radiation imaging system using a portable radiation imaging apparatus capable of fluoroscopic imaging and still image radiographing. FIG. 11A illustrates an example in which the imaging apparatus 100 is detached from a C-type arm 601, and a radiation generating apparatus 206 provided in the C-type arm 601 is used for imaging. Here, the C-type arm 601 holds the radiation generating apparatus 206 and the imaging apparatus 100.

A display unit 602 is a display medium capable of displaying an image based on image data obtained by the imaging apparatus 100. A bed 603 is a board for placing an object 604 thereon. A carriage 605 can move the radiation generating apparatus 206, the imaging apparatus 100, and the C-type arm 601. A portable control apparatus (control computer) 606 can control them.

The control apparatus 606 can also perform image processing on the image signal obtained by the imaging apparatus 100 to transfer image data to the display unit 602 and the like. The image data generated by the image processing by the control apparatus 606 can be transferred to a remote location through a transmission unit such as a telephone line. Accordingly, the image data can be displayed on a display screen in another location such as a doctor room or stored in a storage unit such as an optical disk so as to be used by a remote doctor for diagnosis. The transmitted image data can be recorded as a film by a film processor. Note that some or all of the components of the control circuit unit 108 according to the embodiments of the present invention may be included in the imaging apparatus 100 or in the control apparatus 606. For example, in a case in which the control circuit unit 108 is included in the imaging apparatus 100, the control apparatus 606 may transmit a control signal to the control circuit unit 108.

FIG. 11B illustrates an example of application of the present invention and is a schematic configuration drawing of a radiation imaging system using a portable radiation imaging apparatus capable of fluoroscopic imaging and still image radiographing. Note that the same apparatus configuration as that in FIG. 11A are assigned to the same reference numerals or characters in FIG. 11B and the detailed description thereof will be omitted.

FIG. 11B illustrates an example in which the imaging apparatus 100 is detached from the C-type arm 601, and a radiation generating apparatus 607 different from the radiation generating apparatus 206 provided in the C-type arm 601 is used for imaging. Thus, when another radiation generating apparatus 607 is used for imaging, synchronous imaging can be performed by detecting the start or the end of X-ray irradiation without communication between the radiation generating apparatus 607 and the imaging apparatus 100 through a cable or radio.

Note that the embodiments of the present invention can be achieved, for example, by causing the computer to execute a program. Further, a unit for supplying the computer with the program such as a computer-readable storage medium such as a CD-ROM storing the program or a transmission medium such as the Internet for transmitting the program can also be applied as the embodiment of the present invention. Furthermore, the program can also be applied as the embodiment of the present invention. The program, the storage medium, the transmission medium, and the program are included in the category of the present invention. According to each embodiment of the present invention, the digital data processing unit 105 of the imaging apparatus 100 performs correction processing, but the present invention is not limited to this. For example, an image processing apparatus outside the imaging apparatus 100 of the control apparatus 606 may perform correction processing. Any invention by a combination easily conceivable from each embodiment of the present invention is also included in the category of the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-116271, filed May 24, 2011, which is hereby incorporated by reference herein in its entirety.

The invention claimed is:

1. An imaging apparatus comprising:
a detecting unit, configured to convert radiation or light into an electric signal, provided with a plurality of pixels arranged in a plurality of rows and a plurality of columns, each of the pixels including a conversion element and a transistor;
a drive circuit unit configured to control conducting states of the transistors of the plurality of pixels row by row; and
a control circuit unit configured to control the drive circuit unit based on the electric signal converted by the detecting unit,
wherein the control circuit unit is configured to control the drive circuit unit to perform:
(1) a first operation such that the drive circuit unit sets transistors in a first row and in a second row simultaneously at conducting states, where the first row and the second row are not directly adjacent and where no row adjacent to the first row or the second row is set at the conducting state;
(2) a second operation such that the drive circuit unit sets transistors in a plurality of rows at a non-conducting state, based on a determination of a start of or an end of an irradiation of the radiation or light, based on a comparison, with a threshold, of the electric signal obtained from the detecting unit by the first operation, where the plurality of rows set at the non-conducting state is different from the first row and the second row;
(3) a third operation such that the drive circuit unit sets transistors in another plurality of rows at the conducting state row by row, to acquire an image based on a signal accumulated in the plurality of pixels by the second operation, where the another plurality of rows includes the first row, the second row and the plurality of rows set at the non-conducting state by the second operation;
(4) a fourth operation such that, following subjecting the detecting unit to the third operation, the drive circuit unit sets the transistors in the first row and in the second row simultaneously at the conducting state, where no row adjacent to the first row or the second row is set at the conducting state;
(5) a fifth operation such that, following subjecting the detecting unit to the fourth operation, the drive circuit unit sets the transistors in the plurality of rows at the non-conducting state under a condition without irradiation of radiation or light, where the plurality of rows set at the non-conducting state is different from the first row and the second row; and
(6) a sixth operation such that the drive circuit unit sets the transistors in the another plurality of rows at the conducting state row by row to acquire an offset image based on the signal accumulated in the plurality of pixels by the fifth operation for subtraction processing of the image, where the another plurality of rows includes the first row, the second row and the plurality of rows set at the non-conducting state by the fifth operation.

2. The imaging apparatus according to claim 1, wherein the control circuit unit includes a comparator for performing the determination and a controller for controlling the drive circuit unit based on the determination, and
the control circuit unit controls the drive circuit unit to maintain the transistors of the first row and the second row at the conducting state, and to maintain at the non-conducting state the transistors of the plurality of rows, in response to the determination by the comparator of the start of the irradiation of the radiation or light.

3. The imaging apparatus according to claim 1, wherein the control circuit unit includes a comparator for performing the determination and a timing generating unit for controlling the drive circuit unit based on the determination, and
the control circuit unit controls the drive circuit unit to change the transistors of the first row and the second row into a non-conducting state, when the comparator determines the end of the irradiation of the radiation or light.

4. The imaging apparatus according to claim 1, wherein a source or drain electrode of the transistor is connected to an electrode of the conversion element.

5. The imaging apparatus according to claim 1, further comprising a signal processing unit configured to add or average signals outputted from the transistors of the first row and the second row, wherein the signal processing unit includes a read out circuit performing the adding or averaging the electric signals outputted from the transistors arranged in a column direction.

6. The imaging apparatus according to claim 1, wherein the pixels of a row of the detecting unit are grouped into a plurality of groups.

7. The imaging apparatus according to claim 1, wherein the pixels of the first row and the second row are arranged at outermost rows of the detecting unit.

8. The imaging apparatus according to claim 1, wherein the drive circuit unit is capable of changing the driving of transistors of a plurality of non-continuous rows including the first row and the second row.

9. The imaging apparatus according to claim 8, wherein the drive circuit unit is capable of changing the driving of the transistors of the plurality of non-continuous rows including the first row and the second row, according to an input by user.

10. The imaging apparatus according to claim 1, wherein the drive circuit unit is capable of changing the driving of the transistors of a plurality of non-continuous rows including the first row and the second row, according to a portion of an object for imaging.

11. The imaging apparatus according to claim 1, further comprising a correcting unit for defect correction of the pixels of a plurality of non-continuous rows including the first row and the second row based on the pixels of rows adjacent to the plurality of the non-continuous rows.

12. An imaging system comprising:
the imaging apparatus according to claim 1; and
a controlling computer for transmitting a control signal to the control circuit unit.

13. A driving method of an imaging apparatus including a detecting unit for converting radiation or light into an electric signal provided with a plurality of pixels arranged in a plurality of rows and a plurality of columns, each of the pixels including a conversion element and a transistor; and a drive circuit unit for controlling conducting states of the transistors of the plurality of pixels row by row, the driving method comprising the steps of:

(1) a first step such that the drive circuit unit sets transistors in a first row and a second row simultaneously at conducting states, where the first row and the second row are not directly adjacent and where no row adjacent to the first row or the second row is set at the conducting state;

(2) a second step such that the drive circuit unit sets transistors in a plurality of rows at a non-conducting state, based on a determination of a start of or an end of the irradiation of the radiation or light, based on a comparison, with a threshold, of an electric signal obtained from the detecting unit in the first step, where the plurality of rows set at the non-conducting state is different from the first row and the second row;

(3) a third step such that the drive circuit unit sets transistors in another plurality of rows at the conducting state row by row, to acquire an image based on a signal accumulated in the plurality of pixels in the second step, where the another plurality of rows includes the first row, the second row and the plurality of rows set at the non-conducting state in the second step;

(4) a fourth step such that, following subjecting the detecting unit to the third step, the drive circuit unit sets the transistors in the first row and the second row simultaneously at the conducting state, where no row adjacent to the first row or the second row is set at the conducting state;

(5) a fifth step such that, following subjecting the detecting unit to the fourth step, the drive circuit unit sets the transistors in the plurality of rows at the non-conducting state, under a condition without irradiation of radiation or light, where the plurality of rows set at the non-conducting state is different from the first row and the second row; and (6) a sixth step such that the drive circuit unit sets the transistors in the another plurality of rows at the conducting state row by row to acquire an offset image based on the signal accumulated in the plurality of pixels in the fifth step for subtraction processing of the image, where the another plurality of rows includes the first row, the second row and the plurality of rows set at the non-conducting state in the fifth step.

* * * * *